(12) United States Patent
Inoue et al.

(10) Patent No.: US 6,894,297 B1
(45) Date of Patent: May 17, 2005

(54) MULTI-COMPONENT GAS ANALYZING METHOD USING FTIR

(75) Inventors: Kaori Inoue, Kyoto (JP); Masayuki Adachi, Kyoto (JP)

(73) Assignee: Horiba, Ltd., Miyanohigashi-machi (JP)

( * ) Notice: Subject to any disclaimer, the term of this patent is extended or adjusted under 35 U.S.C. 154(b) by 0 days.

(21) Appl. No.: 09/578,998

(22) Filed: May 25, 2000

(30) Foreign Application Priority Data

Jun. 4, 1999 (JP) .......................................... 11-158493

(51) Int. Cl.[7] .............................. G21G 4/00; G01J 5/02
(52) U.S. Cl. .............................. 250/493.1; 250/339.08; 73/1.06; 356/319
(58) Field of Search ........................ 250/493.1, 339.08; 73/1.06, 106.1; 356/319

(56) References Cited

U.S. PATENT DOCUMENTS

| | | | |
|---|---|---|---|
| 5,138,163 A | | 8/1992 | Butler et al. |
| 5,305,076 A | | 4/1994 | Inoue et al. |
| 5,351,198 A | * | 9/1994 | Adachi et al. ............... 356/319 |
| 5,838,008 A | * | 11/1998 | Esler et al. ............ 250/339.08 |
| 6,297,504 B1 | * | 10/2001 | Andreou ..................... 250/330 |
| 6,370,936 B1 | * | 4/2002 | Yamagishi et al. .......... 73/1.35 |
| 6,422,056 B1 | * | 7/2002 | Miyai et al. ................. 73/1.06 |

FOREIGN PATENT DOCUMENTS

| | | |
|---|---|---|
| DE | 42 03 588 A1 | 8/1992 |
| DE | 692 04 000 T2 | 3/1993 |
| DE | 43 17 867 A1 | 12/1994 |

\* cited by examiner

*Primary Examiner*—John R. Lee
*Assistant Examiner*—Paul M. Gurzo
(74) *Attorney, Agent, or Firm*—Raysman Millstein Felder & Steiner LLP (57) ABSTRACT

The present invention provides a multi-component gas analyzing method using FTIR, which can correct for an influence of a coexistent gas due to an intensity change in the spectrum itself that occurs depending on the base gas composition so that it is possible to carry out, a measurement with high precision. A plurality of components in a sample are quantitatively analyzed based upon an absorption spectrum obtained by FTIR. After having calculated multi-component concentrations from a mixed gas spectrum by using a quantitative algorithm, calculations are further carried out so as to correct for a change in spectrum due to a coexistent gas component with respect to part of target components.

19 Claims, 7 Drawing Sheets

CO peak intensity (calculated value)

MULTI-COMPONENT GAS ANALYZING METHOD USING FTIR

FIELD OF THE INVENTION

The present invention relates to a multi-component gas analyzing method using FTIR (Fourier Transform Infrared Spectroscopy), which executes a quantitative analysis on a plurality of components in a sample based upon an absorption spectrum obtained by FTIR.

DESCRIPTION OF PRIOR ART

Figure 1:
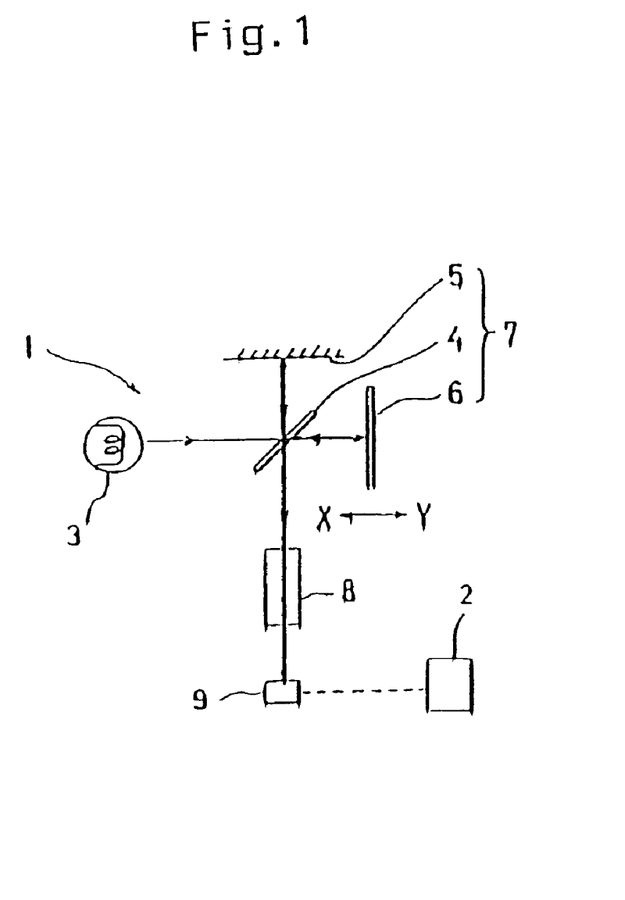
FIG. 1 is a schematic view showing one sample of a device for carrying out the method of the present invention.

FIG. 1 is a schematic view showing the structure of a gas analyzer (hereinafter, referred to as FTIR gas analyzer) that uses a Fourier transform infrared spectroscopy conforming to FTIR. In FIG. 1, reference number 1 is an analyzing section, reference number 2 represents a data processing section for processing interferrograms, which is an output of the analyzing section 1.

The analyzing section 1 is constituted by an interference mechanism 7 consisting of an infrared light source 3 arranged to emit parallel infrared light rays, a beam splitter 4, a fixed mirror 5 and a movable mirror 6 that is allowed to make parallel movements, for example, in X-Y directions by a driving mechanism installed outside FIG. 1, a cell 8 in which a test sample, a reference sample, etc. are placed and to which the infrared light rays from the infrared light source 3 are directed through the interference mechanism 7, and a semiconductor detector 9, etc.

Here, the data processing section 2, which is formed by, for example, a computer, is arranged to average the interferrogram, transform the averaged interferrogram into absorption spectrum by fast Fourier transformation and carry concentration calculations on target components based upon the absorption spectrum.

In the FTIR gas analyzer arranged as described above, a plurality of components are quantitatively analyzed in the following manner. Reference samples or test samples are respectively flowed into the cell 8, and infrared rays from the infrared light source 3 are directed to the cell 8 so that interferrograms of the reference samples or the test samples are measured. These interferrograms are respectively Fourier-transformed in the data processing section 2 to obtain a power spectrum. Then, the ratio of the power spectrum of the test sample to the power spectrum of the reference sample is calculated, and an absorption spectrum is obtained by converting the ratio into the absorbance scale. Thereafter, a plurality of components contained in the test sample are quantitatively analyzed based upon absorbances of a plurality of wave number points in the absorption spectrum.

With respect to the method for quantitatively analyzing a plurality of components, for example, the applicant of the present application have proposed several methods in the specifications of the following Japanese Patents (JP Nos.: 2649667, 2741376, 2926277, and 2926278). For example, JP No. 2649667 discloses a multi-component analyzing method in which the sum of relative absorbances, each representing a difference between a local peak value and a local valley value in each point of a plurality of wave number points in the absorption spectrum, is found. Based upon the sum, concentrations of a plurality of components are respectively obtained independently.

In addition to the above-mentioned methods, with respect to the quantitative analysis on multi-components, quantitative algorithms for multi-variable analysis, such as PLS (Partial Least Square), PCR (Principal Component Regression) etc., may be used. In any of these methods, concentration operating data (calibration matrix) are preliminarily prepared based upon, a calibration spectrum having a known concentration, and by applying the calibration matrix for a in sample spectrum having an unknown concentration, concentrations of a plurality of components in the sample spectrum are calculated individually.

Figure 6:
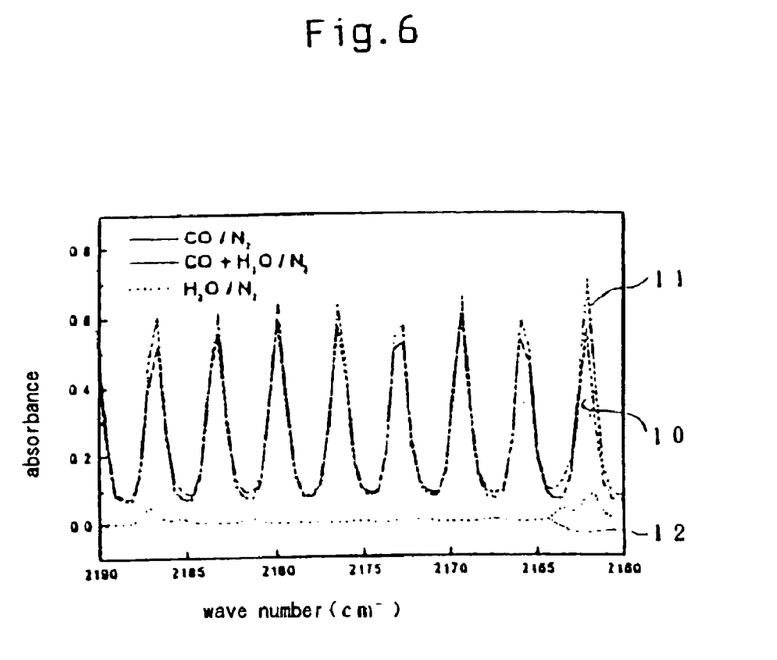
FIG. 6 is a graph that explains conventional problems.

However, in the case of measurements on engine exhaust gases by the use of the above-mentioned FTIR, it is generally known that if the generally used quantitative algorithm, such as PLS, PCR, etc., is applied, the readings of CO, $CO_2$ and NO become higher than the actual concentrations due to an influence of high concentration of $H_2O$ commonly existing in a sample gas at the time of an actual measurement of the sample gas. This is not due to the interference that occur by an insufficient separation of overlapped spectra even by the use of the quantitative algorithm, but is due to the fact that there is a difference in the spectrum intensity itself, for example, as shown in FIG. 6, even in the case of the same component and the same concentration, depending on the base gas composition. More specifically, this is because CO in an actual sample gas which contains both $N_2$ and $H_2O$, as it were ($N_2+H_2O$) base gas, shows a greater absorption spectrum than CO in the span gas containing only $N_2$ as a base component. In FIG. 6, reference numbers 10, 11 and 12 show the respective absorption spectra of CO, (CO+$H_2O$) and $H_2O$ when $N_2$ gas is used as a base gas. Additionally, the same phenomenon can be observed even in the coexistence of $O_2$, $H_2$ which have no infrared-ray absorption.

Figure 7:
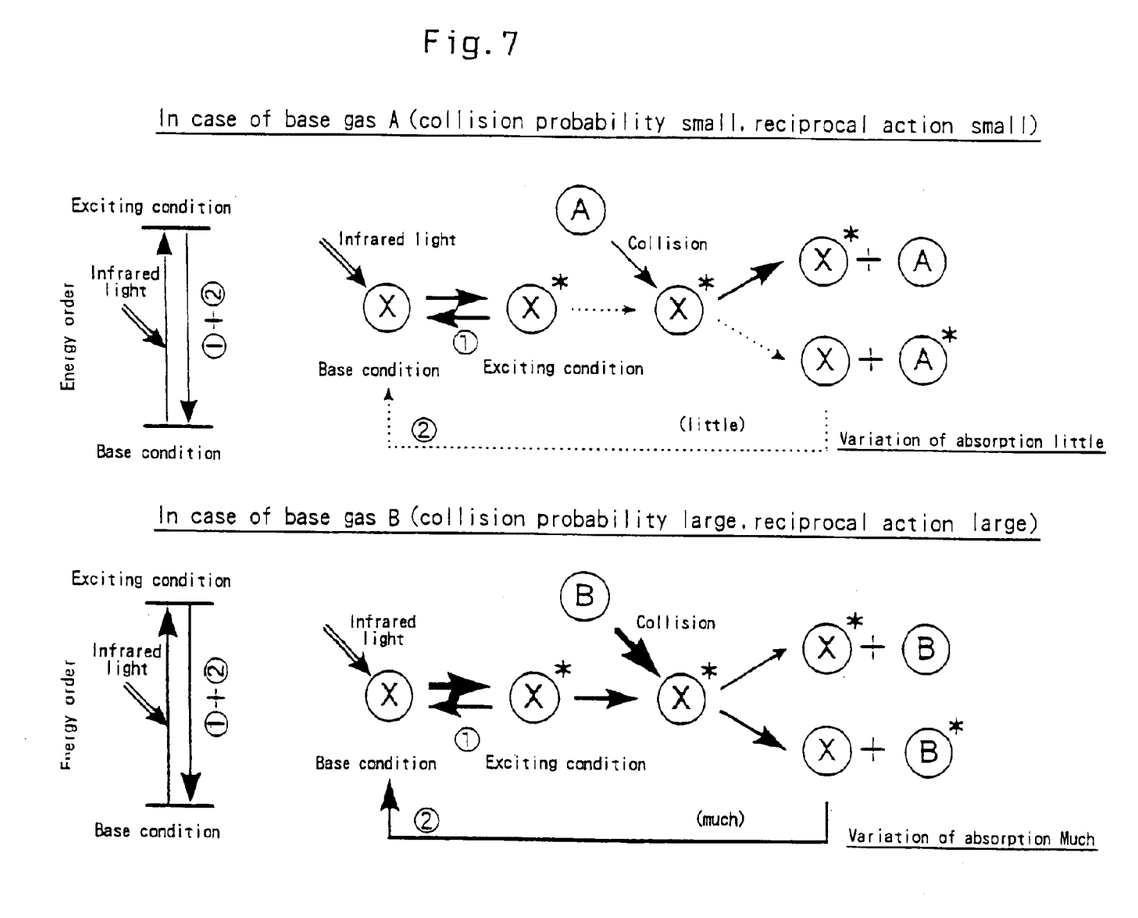
FIG. 7 is a model illustrating changes in the amount of infrared absorption due to quenching.

Although an actual mechanism of the above-mentioned phenomenon is not clearly understood, it is considered that quenching due to interactions between gas molecules might relate to this phenomenon as one of the reasons. FIG. 7 is a model illustrating changes in the amount of infrared absorption due to quenching, and this model indicates that changes in the amount of infrared absorption occur depending on the degree of probable collision between a gas component X and a base gas and the interaction between them. In other words, FIG. 7(A) shows a case in which both the possibility of collision and the interaction of a base gas A to the gas component X are small. In this case, hardly any effects are given to the equilibrium of the basic condition and excited condition of gas component X so that the existence of the base gas A hardly gives any effects on the amount of absorption of the gas component X. Moreover, FIG. 7(B) shows a case in which both the possibility of collision and the interaction of the base gas B to the gas component X are great. In this case, since the equilibrium or the gas component X is shifted to the basic condition side, additional light absorption is more likely to occur. In other words, the existence of the base gas B increases the absorption intensity of the gas component X, thereby providing a stronger absorption as compared with the case of the base gas component A. In the example shown in FIG. 6, $N_2$ represents components A, $H_2O$ represents component B and CO represents component X.

Moreover, another possible mechanism is "collision expansion" in which the line width of the absorption spectrum is widened due coexistence with another component.

SUMMARY OF INVENTION

The present invention has been devised to solve the above-mentioned problems, and its objective is to provide a multi-component gas analyzing method using FTIR, which can correct for an influence of a coexistent gas due to an intensity change in the spectrum itself that occurs depending on the base gas composition so that it is possible to carry out a measurement with high precision.

In order to achieve the above-mentioned objective in a multi-component gas analyzing method using FTIR of the present invention, a plurality of components in a sample are quantitatively analyzed based upon an absorption spectrum obtained by FTIR. After having calculated multi-component concentrations from a mixed gas spectrum by using a quantitative algorithm, calculations are further carried out so as to correct for a change in spectrum due to a coexistent gas component with some target components.

Upon carrying out the above-mentioned correcting calculations, if the coexistent gas component is measured by FTIR, the measured results can be used. In this case, there is no time delay among the measured values. Moreover, if the coexistent gas component is not measured by FTIR, the corresponding data may be read from an external analyzer and used, and in this case, time matching may be made in the CPU of the FTIR.

In accordance with the multi-component gas analyzing method using FTIR of the present invention, it is possible to correct an error caused by an intensity change in the spectrum itself which can not be considered by a normal quantitative algorithm, and consequently, to improve the precision of a gas analysis using FTIR. In particular, the present invention is effectively used for correcting influences due to a difference in the base gas composition between an exhaust gas and a calibration gas, that is, in particular, a difference in $H_2O$ concentration and a change in the $H_2O$ concentration in a sample gas being measured.

BRIEF DESCRIPTION OF THE DRAWINGS

FIG. 2 are exemplary graphs showing the influence of coexistent of $H_2O$ with respect to the CO 10% range, wherein FIG. 2(A) shows the case of fixed CO concentration and FIG. 2(B) shows the case of fixed $H_2O$ concentration;

FIG. 4 are graphs showing the relationship between the CO concentration (calculated values) and the error, wherein FIG. 4(A) shows a state before the correction and FIG. 4(B) shows a state after the correction;

FIG. 5 are graphs showing variations in the influenced value in the CO 10% range, wherein FIG. 5(A) shows actual data and FIG. 5(B) shows data after having been standardized;

DETAILED DESCRIPTION OF THE PREFERRED EMBODIMENTS

Referring to FIGS. 1–7, the following description will discuss embodiments of the present invention. As described above, the measurement of an actual sample gas is greatly influenced by $H_2O$ contained therein. Therefore, an explanation will be given of an exemplary of examination on correction expression correcting the influence of coexistent $H_2O$ which is a component that can be measured by FTIR on CO or other components after concentration calculations carried out by a multivariable analyzing method. Here, it is taken as a premise that influences caused by components other than $H_2O$ are actually negligible.

Figure 2:
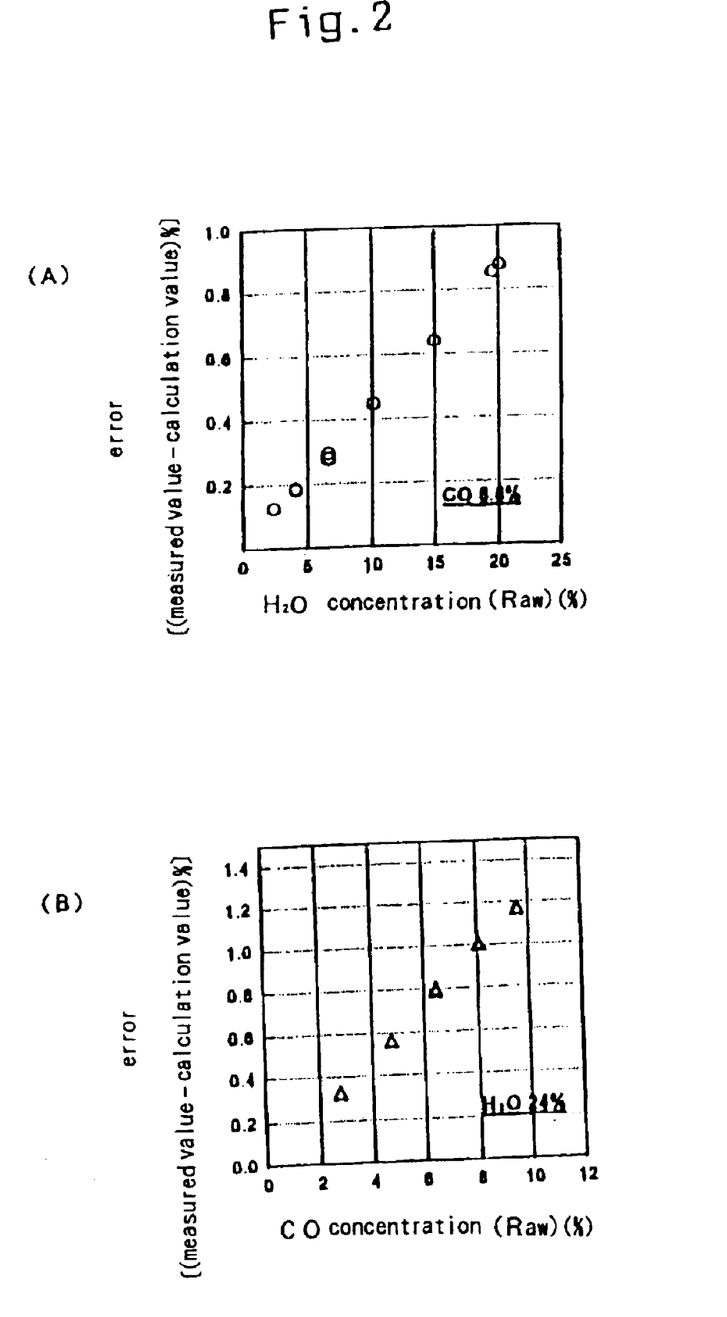

1. Examination on Correction Expression (1) Confirmation of Trend of Influenced Value FIG. 2 are exemplary graphs showing the influence of coexistent $H_2O$ with respect to the CO 10% range (calculated by raw concentration values before linearizing), wherein FIG. 2(A) shows the case for a fixed CO concentration and FIG. 2(B) shows the case for a fixed $H_2O$ concentration. As shown by FIG. 2 for the fixed $H_2O$ concentration, the influence can be approximated by a linear equation (Y=aX). In some cases, depending on the components, the influence may be better approximated by a quadratic equation (Y=aX$^2$+bX).

(2) Model of Influence and Correction Expression

Figure 3:
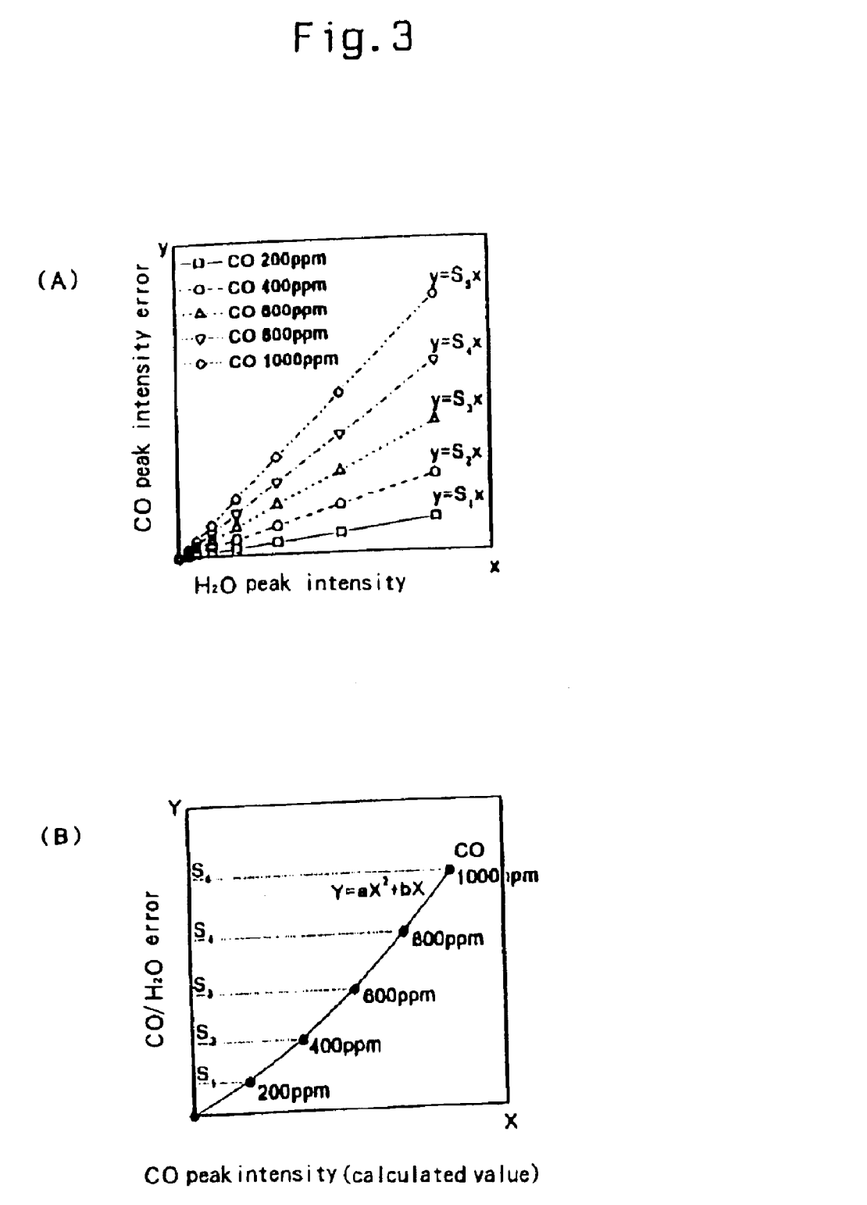
FIG. 3(A) is a graph that shows a model of the influence on CO and $H_2O$.
FIG. 3(B) is a graph that shows one example of a correction expression.

FIG. 3 shows examples of a model of influence and a correction expression in CO and $H_2O$. In this model, it is supposed that the peak intensity of $H_2O$ (nearly equal to calculated concentration value before linearizing) x (=W) and a change in the peak intensity of CO, (a change in concentration calculated value before linear rise) y have a relationship represented by a linear equation (y=Sx). The inclination S of this linear equation changes in proportion to the peak intensity of CO as shown in FIG. 3(A). The relationship between the inclination S (=Y) and the peak intensity X (=C) of CO without influence of $H_2O$ is approximated by a quadratic equation (Y=aX$^2$+bX), as shown in FIG. 3(B). Here, the CO concentration value R, obtained by the conventional PCR, is represented by:

$$R=y+X=\{(aX^2+bX)Xx\}+X$$

By solving this equation with respect to X (=C), a relational expression for finding the peak intensity of CO in which the influence of $H_2O$ is corrected is obtained.

In the above-mentioned method, in order to obtain correction coefficients a and b, data shown in FIG. 3(B), that is, actual measured values of the influence of coexistence at the time when only the CO concentration is changed with the $H_2O$ concentration being virtually fixed (data at the time when the $H_2O$ concentration is changed are not necessary), are used.

Then, the CO concentration (before linearizing) C after correction is represented as follows:
when a=0 (Y=bX), C=R/(1+bW)
when a≠0 (Y=aX$^2$+bX),
C=[√{(1+bW)$^2$+4aWR}−(1+bW)]/2aW
where R: CO concentration (before linearizing) prior to correction, W: $H_2O$ concentration (before linearizing).

(3) Example of Result of Correction

Figure 4:
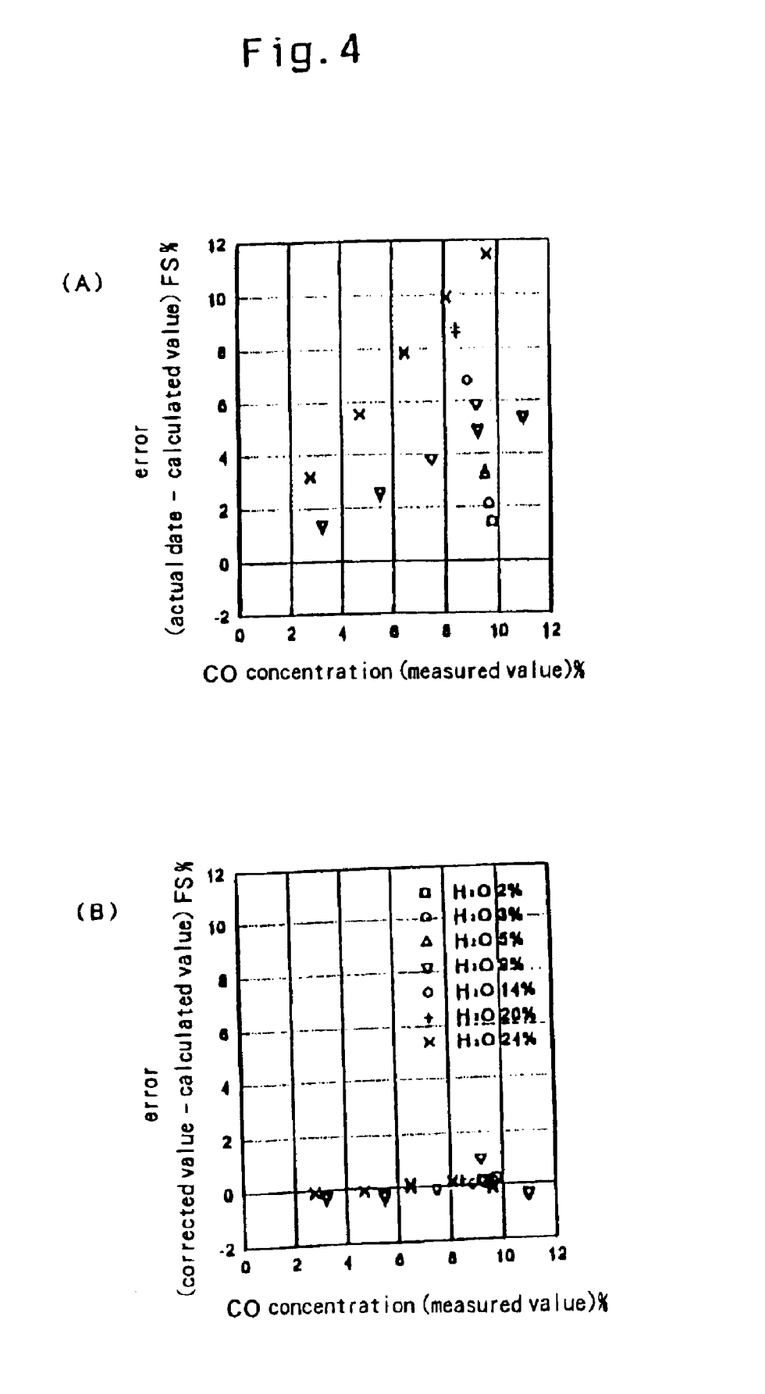

FIG. 4 are graphs showing an example (CO 10% range) of correction made by the expression shown in FIG. 2, wherein FIG. 4(A) shows data before the correction and FIG. 4(B) shows data after the correction. As a result of this correction method, the influenced value, which is approximately 12% at maximum (full scale, FS), is maintained within a range of ±1% or slightly more.

2. Confirmation of Difference in Devices

It is necessary to decide how to take actual data for determining coefficients for each of devices based upon variation of the absolute value and trend of the influence of coexistent $H_2O$. Therefore, three devices were used so as to confirm the variations and the possibility of simplification for the correction method.

(1) Confirmation of Trend of Influenced Values

Figure 5:
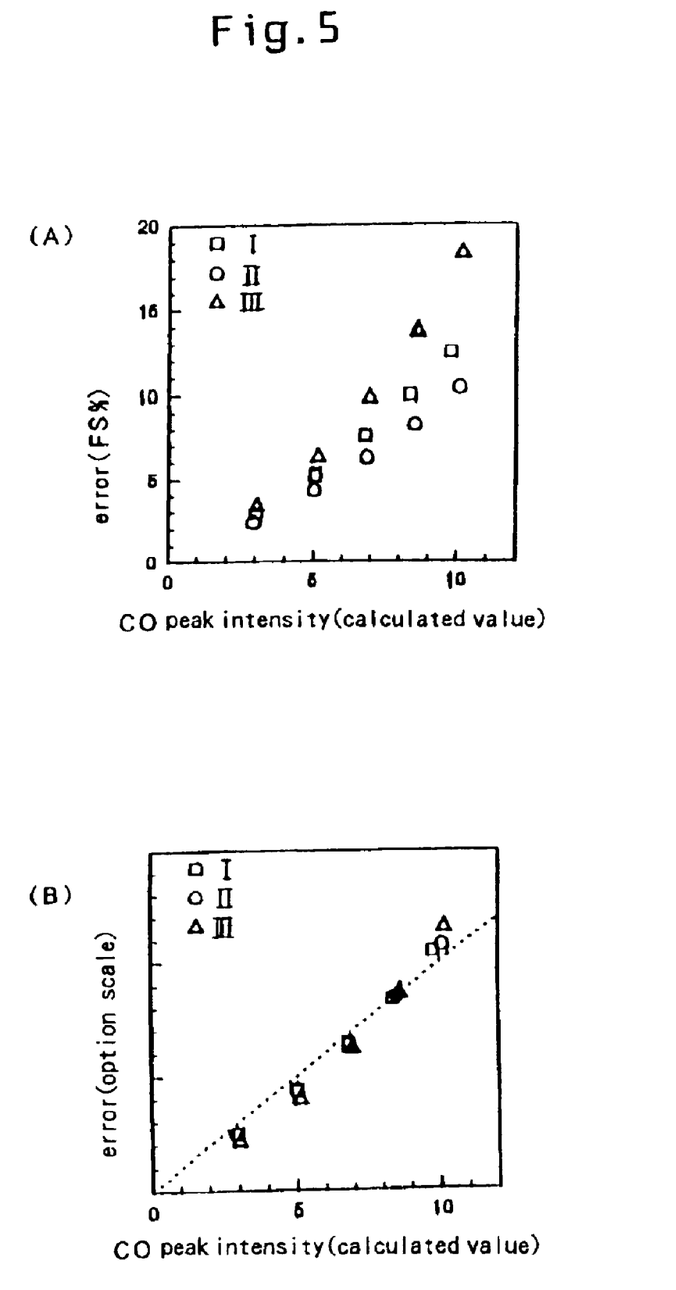

FIG. 5 are graphs showing variations in influenced values in the CO 10% range, wherein FIG. 5(A) shows the relationship between the CO peak intensity and errors in actual data (CO 10%) and FIG. 5(B) shows the relationship between the CO peak intensity and errors in a standardized state (CO 10%). As shown in FIG. 5, although there are considerable gaps in terms of absolute values, there is a common trend. It is considered that one of the reasons for variations is a difference in wave number points used in calculation for PCR in each of the devices.

Moreover, the following Table 1 shows variations in influence in which other components were included. Table 1 indicates that CO, $CO_2$, NO and $N_2O$ are subjected to great influences, and with respect to these, since the width of variations is great, the correction coefficient needs to be determined for each device.

TABLE 1

| Component | Range | Influence (error, FS %) A | B | C | Average (FS %) | Maximum Deviation (FS %) |
|---|---|---|---|---|---|---|
| CO | 200 ppm | 6.3 | 5.6 | 7.3 | 6.4 | 0.9 |
|  | 1000 ppm | 8.5 | 7.3 | 9.5 | 8.4 | −1.1 |
|  | 5000 ppm | 9.0 | 8.1 | 11.9 | 9.6 | 2.2 |
|  | 2% | 9.9 | 8.0 | 13.7 | 10.5 | 3.2 |
|  | 10% | 12.7 | 10.3 | 18.0 | 13.7 | 4.3 |
| $CO_2$ | 1% | 10.3 | 11.0 | 8.0 | 9.8 | −1.8 |
|  | 5% | 9.0 | 7.3 | 7.4 | 7.9 | 1.1 |
|  | 20% | 11.7 | 11.9 | 3.6 | 9.0 | −5.5 |
| NO | 200 ppm | 3.7 | 3.1 | 5.0 | 3.9 | 1.1 |
|  | 1000 ppm | 6.7 | 6.0 | 9.5 | 7.4 | 2.1 |
|  | 5000 ppm | 8.7 | 9.0 | 11.4 | 9.7 | 1.7 |
| $N_2O$ | 200 ppm | 5.1 | 5.2 | 7.2 | 5.8 | 1.4 |
| $NH_3$ | 500 ppm | 5.1 | 3.4 | 2.3 | 3.6 | 1.5 |
| $SO_2$ | 200 ppm | −.24 | 0.9 | −4.4 | −1.9 | 2.9 |
| $CH_3OH$ | 500 ppm | 3.6 | 3.2 | 1.9 | 2.9 | −1.0 |
|  | 2000 ppm | 2.4 | 1.5 | 0.7 | 1.5 | −0.9 |
| $CH_4$ | 500 ppm | 1.9 | 1.2 | 1.9 | 1.7 | −0.4 |
| $C_2H_4$ | 500 ppm | 2.8 | 1.1 | −3.1 | 0.3 | −3.3 |
| $C_3H_6$ | 200 ppm | −0.9 | 1.0 | −2.3 | −0.7 | 1.7 |
| $1,3-C_4H_6$ | 200 ppm | 2.1 | 1.2 | −1.6 | 0.6 | −2.2 |
| iso-$C_4H_8$ | 200 ppm | −0.4 | 1.5 | −3.5 | −0.8 | −2.7 |

(2) Simplification of Correction

With respect to the measurement results of the three devices A to C shown in Table 1, an explanation will be given of the results of corrections made on components, CO, $CO_2$ and NO. In these cases, the following three correction methods are suggested:

(a) A quadratic equation (a≠0 in FIG. 3) is used as a correction coefficient, and this is determined for each of the devices.

(b) A quadratic equation (a≠0 in FIG. 3) is used, and based on the correction coefficient of one of the three devices A, B, C, the inclination is adjusted for each of the devices.

(c) A linear equation (a=0 in FIG. 3) is used as a correction coefficient, and this is determined for each of the devices.

The following description will discuss the respective correction methods and the results thereof:

(a) In the case where the correction coefficient (quadratic equation) is determined for each device.

Five data points (⅕ division point to ⅗ division point) of Wet ($N_2+H_2O$ base) span spectra were sampled for each of the components of CO, $CO_2$, and NO. Based upon the data points, the correction coefficient was determined for each device.

The results thereof are shown in Table 2.

TABLE 2

| Component | Range | Influenced Value (FS %) A | B | C |
|---|---|---|---|---|
| CO | 200 ppm | 0.1 | −1.2 | 0.3 |
|  | 1000 ppm | 0.2 | 0.4 | 0.3 |
|  | 5000 ppm | 0.2 | 0.1 | 0.1 |
|  | 2% | 0.1 | −0.1 | 0.2 |
|  | 10% | 0.1 | 0.1 | 0.3 |
| $CO_2$ | 1% | 0.1 | 0.2 | 0.3 |
|  | 5% | 0.1 | 0.2 | 0.2 |
|  | 20% | 0.1 | 0.1 | −0.2 |
| NO | 200 ppm | 0.3 | −0.4 | 0.4 |
|  | 1000 ppm | −0.1 | 0.2 | 0.2 |
|  | 5000 ppm | 0.2 | 0.3 | 0.2 |

(b) In the case where only the inclination is adjusted by using the same coefficient (quadratic equation).

Among data of the respective devices used in Table 2, the correction coefficient (quadratic equation) for device A is revised and used based upon a single data point (⅘ division point). The results from the corrections of the remaining four data points are evaluated. The results thereof are shown in Table 3. Here, the results related to device A are the same as those in Table 2.

TABLE 3

| Component | Range | Influenced Value (FS %) A | B | C |
|---|---|---|---|---|
| CO | 200 ppm | 0.1 | −2.4 | −0.8 |
|  | 1000 ppm | 0.2 | −1.2 | −0.5 |
|  | 5000 ppm | 0.2 | −0.2 | −0.3 |
|  | 2% | 0.1 | 0.3 | −0.6 |
|  | 10% | 0.1 | 0.2 | 0.9 |
| $CO_2$ | 1% | 0.1 | −0.2 | −1.0 |
|  | 5% | 0.1 | −0.3 | −0.2 |
|  | 20% | 0.1 | 0.3 | −0.5 |
| NO | 200 ppm | 0.3 | −0.6 | −1.0 |
|  | 1000 ppm | −0.1 | −0.3 | −0.5 |
|  | 5000 ppm | 0.2 | 1.0 | −0.4 |

(c) In the case where the linear equation is used to correct each of the devices.

The correction coefficient (linear equation) was determined by using only a single data point (⅘ division point) among data of the respective devices used in Table 2. The results from correcting the remaining four points are evaluated. The results thereof are shown in Table 4.

TABLE 4

| Component | Range | Influenced Value (FS %) A | B | C |
|---|---|---|---|---|
| CO | 200 ppm | −0.6 | −1.9 | −0.8 |
|  | 1000 ppm | −0.5 | −1.6 | −1.0 |
|  | 5000 ppm | −0.4 | −0.4 | −0.6 |
|  | 2% | −0.6 | −0.4 | −1.2 |
|  | 10% | −0.7 | 0.5 | −1.4 |
| $CO_2$ | 1% | 1.3 | −1.5 | −1.1 |
|  | 5% | 0.2 | −0.4 | −0.3 |
|  | 20% | 0.3 | −0.3 | −0.6 |
| NO | 200 ppm | −0.6 | −0.8 | −0.9 |
|  | 1000 ppm | −0.6 | −0.8 | −0.7 |
|  | 5000 ppm | −0.6 | −0.6 | −0.8 |

Tables 2 to 4 show that, even in the case of the linear equation (c), the results of the correction are maintained within a width of approximately ±2%. Consequently, it is possible to make corrections even by sampling only a single data point of actual data for each component/range.

As described above in the present invention, in a multi-coefficient gas analyzing method using FTIR in which a plurality of components in a sample are quantitatively analyzed based upon an absorption spectrum obtained by FTIR, after having calculated multi-component concentrations, from a mixed gas spectrum by using a multi-variable analyzing method, etc., calculations are further carried out so as to correct a change in spectrum due to a coexistent gas component with respect to some target components. Therefore, it is possible to correct an error caused by an intensity change in the spectrum itself which can not be corrected by a normal quantitative algorithm and, consequently, to improve the precision of a gas analysis using FTIR.

In particular, for example, in the case of $H_2O$ where the correction is made by using a, measured values obtained in FTIR, the method is advantageous because the time delay among measured values for the respective components are negligible. Moreover, with respect to components such as $O_2$ and $H_2$ that are components which FTIR fails to measure in principle, signals taken from an external analyzer can be time-matched in the CPU of the FTIR and then used in the correction. Thus, it is possible to obtain the same effects.

The multi-component gas analyzing method of the present invention is effectively used for correcting the influence caused by a difference in water concentration between exhaust gases and a calibration gas and a change in $H_2O$ concentration in a sample gas being measured. The method also makes it possible to correct influences caused by $O_2$ and $H_2$.

What is claimed is:

1. A multi-component gas analyzing method using FTIR, comprising:
   quantitatively analyzing a plurality of components in a sample based upon an absorption spectrum obtained by FTIR;
   calculating multi-component concentrations from a mixed gas spectrum by using a quantitative algorithm; and
   correcting for an error in the calculated multi-component concentrations caused by a change in an intensity spectrum obtained by FTIR due to a presence of a coexistent gas in the sample.

2. The method of claim 1, further comprising:
   measuring the coexistent gas component using FTIR; and
   directly applying resulting data from the correcting calculations.

3. The method of claim 1, further comprising:
   measuring the coexistent gas component using a method other than FTIR; and
   using an external analyzer to read resulting data from the correcting calculations, wherein time matching is performed by a CPU of the FTIR.

4. The method of claim 1, wherein the correcting step corrects influences of coexistent H2O with respect to CO, CO2, NO, and N2O.

5. The method of claim 4, wherein the influence is approximated by a linear equation for a fixed H2O concentration.

6. The method of claim 4, wherein the influence is approximated by a quadratic equation for a fixed H2O concentration.

7. The method of claim 1, wherein the correcting step corrects influences of coexistent H2O with respect to CO.

8. The method of claim 7, wherein the influence is approximated by a linear equation for a fixed H2O concentration.

9. The method of claim 7, wherein the influence is approximated by a quadratic equation for a fixed H2O concentration.

10. The method of claim 1, wherein the correcting step corrects influences of coexistent H2O with respect to CO2.

11. The method of claim 10, wherein the influence is approximated by a linear equation for a fixed H2O concentration.

12. The method of claim 10, wherein the influence is, approximated by a quadratic equation for a fixed H2O concentration.

13. The method of claim 1, wherein the correcting step corrects influences of coexistent H2O with respect to NO.

14. The method of claim 13, wherein the influence is approximated by a linear equation for a fixed H2O concentration.

15. The method of claim 13, wherein the influence is approximated by a quadratic equation for a fixed H2O concentration.

16. The method of claim 1, wherein the correcting step corrects influences of coexistent H2O with respect to N2O.

17. The method of claim 16, wherein the influence is approximated by a linear equation for a fixed H2O concentration.

18. The method of claim 16, wherein the influence is approximated by a quadratic equation for a fixed H2O concentration.

19. The method of claim 1, wherein the correcting step corrects influence caused by a difference in water concentration between exhaust gases and a calibration gas and a change in H2O concentration in a sample gas being measured.

* * * * *